US00PP08613P

United States Patent [19]

Pieters et al.

[11] Patent Number: Plant 8,613

[45] Date of Patent: Feb. 22, 1994

[54] GUZMANIA PLANT NAMED RED STAR

[76] Inventors: Luc Pieters; Caroline DeMeyer, both of Koewegstraat 4, 9270 Laarme, Belgium

[21] Appl. No.: 25,244

[22] Filed: Mar. 2, 1993

[30] Foreign Application Priority Data

Jul. 9, 1992 [BE] Belgium ..... S1422
Jul. 15, 1992 [NL] Netherlands ..... BRM28

[51] Int. Cl.[5] ..... A01H 5/00
[52] U.S. Cl. ..... Plt./88.8

[58] Field of Search ..... Plt. 88.1, 88.8

*Primary Examiner*—James R. Feyrer
*Attorney, Agent, or Firm*—Cushman, Darby & Cushman

[57] ABSTRACT

A new and distinct variety of Guzmania, named "Red Star", characterized as to novelty by a unique combination of broad leaves; compact foliage; and large, stout and intensely colored, red inflorescence having remarkably wide bracts.

2 Drawing Sheets

BACKGROUND OF THE INVENTION

Our present invention is that of a new and distinct variety of plant in the genus Guzmania within the faily Bromeliaceae, which we have named Guzmania "Red Star".

Plants of the genus Guzmania, especially the species *G. lingulata* and its many varieties and hybrids, have long been desirable, decorative plants due to their long-lasting, ornamental inflorescence and symmetrical foliage. It has been a continuing goal of breeders to produce a compact Guzmania plant with a large, brilliantly-colored inflorescence, which plant would also be fast-growing. This goal has led to the frequent hybridization of *Guzmania lingulata* varieties with *Guzmania wittmackii* varieties. *G. lingulata* contributes relative compactness and brilliant color. *G. wittmackii* contributes a large inflorescence, but also long leaves, large size and an open growth habit. Because *G. lingulata* is a highly variable species, its many cultivars and naturally occurring varieties provide a large gene pool. The remaking of the cross of *G. lingulata* with *G. wittmackii* using different cultivars results in hybrids of the two species being markedly different from one another.

In the course of an ongoing breeding program, we selected for hybridization a variety of *Guzmania minor* which has been designated *G. minor* "No. 5" and a cultivar of *G. wittmackii* which has been designated *G. wittmackii* "No. 8901". *G minor* is considered a botanical variety of *G. lingulata* by many persons; and others consider it a closely related but separate species. Like *G. lingulata, G. minor* is highly variable in phenotype characters.

The progeny of the cross were grown at Laarne, Belgium, and were highly homogenous. One plant particularly exhibiting the distinctive characteristics of the hybrid was selected to constitute the new variety. We have reproduced the selected plant of the new variety asexually at Laarne, Belgium, by division of basal suckers, with characteristics remaining true to type. Subsequent to its asexual reproduction by basal sucker division, the new variety has also been asexually reproduced by us at Laarne, Belgium, by means of tissue culture.

SUMMARY OF THE INVENTION

Our new variety can be readily distinguished from other similar Guzmania hybrids by its broad leaves, compact foliage and large, stout inflorescence. Our new variety is readily distinguishable from its parent species. Foliage length is intermediate compared to the parent species, but the leaves are nearly as wide as *G. wittmackii* "No. 8901". The inflorescence is intermediate in height and in the separation of scape bracts. The length and curvature of scape bracts is indicative of the *G. wittmackii* parentage, but the form of the inflorescence is distinctive.

Guzmania hybrids somewhat like our new variety are Guzmania "Rana" and Guzmania "Cherry", which share the same parent species as our new variety. Our new variety differs considerably from both of these. Guzmania "Cherry" and Guzmania "Rana" are generally similar to one another, but differ from one another in various characteristics, particularly in the color of their inflorescence. Our new variety, Guzmania "Red Star", differs from both of these varieties by having wider leaves, shorter leaves, a shorter inflorescence, and wider scape bracts located more closely together. The leaves of our new variety are approximately 1.5 cm. wider than the leaves of the two referenced varieties when grown under similar horticultural conditions. The leaves of our new variety are approximately 13 cm. shorter than the leaves of G. "Rana" and G. "Cherry" when grown under similar horticultural conditions. The inflorescences of G. "Cherry" and G. "Rana" reach a height above the soil higher than our new variety by approximately 15 cm. or more. The colorful scape bracts of our new variety are approximately 3 cm. wider than those of G. "Cherry" and G. "Rana" when grown under like horticultural conditions. The separation of scape bracts on the stalk of the inflorescence is much greater on the other varieties. For G. "Red Star" the distance separating the scape bracts is approximately 3 cm. along the floral stalk, with the distance between bracts becoming less, proceeding up the inflorescence until the scape bracts are only about 1 cm. or less apart at the top portion of the stalk where floral spikes emerge. In comparison, the scape bracts of G. "Cherry" and G. "Rana" are separated by approximately 7 cm. and the distance between bracts remains more than twice the separation of G. "Red Star", proceeding up the inflorescence.

BRIEF DESCRIPTION OF THE DRAWINGS

The accompanying photographs clearly depict the new variety.

FIG. 1 shows Guzmania "Red Star" in full bloom, particularly highlighting the compactness of both the foliage and the inflorescence. These characteristics are particularly notable in comparison to the illustrations of G. "Rana" accompanying the Letters Patent for that variety (U.S. Plant Pat. No. 7471, Mar. 12, 1991).

FIG. 2 shows a close-up view of the inflorescence of the new variety.

DETAILED DESCRIPTION

The following is a detailed description of our new variety, based on observations of specimens grown in our greenhouse in Laarne, Belgium. Physical characteristics may vary in accordance with cultural conditions, such as light intensity, fertilization programs, temperature, day lengths, humidity and other cultural factors.

I. Parentage: A hybrid of a cultivar of *Guzmania minor* (sometimes a/k/a/ *Guzmania lingulata* v. minor) designated as *Guzmania minor* "No. 5", crossed with a cultivar of *Guzmania wittmackii* designated as *Guzmania wittmackii* "No. 8901".

II. Propagation: Holds its distinguishing characteristics through succeeding generations of asexually reproduced plants.

III. Form: Rosette.

IV. Growth: A comparatively fast-growing plant within the genus Guzmania. Under growing conditions prevailing in Belgium (cooler and lower light intensity compared to conditions prevailing in Central and Southern Florida and Southern California, the current centers for commercial growing of the bromelaids in the United States of America), the plant can be raised from tissue-cultured micro-cutting to a plant in full bloom in 33 months. A tissue-cultured micro-cutting will grow to transplantable plantlet size in seven months, without fertilizer. An additional 10 months is required to reach standard commercially saleable size. After an additional 13 months of growth, the plant can be artificially induced to bloom by application of acetylene. Full flowering occurs within three months thereafter. The vigorous growth rate of our new variety is similar to that of G. "Rana" and G. "Cherry", and faster than varieties not exhibiting hybrid vigor. Resistance to disease organisms appears to be similar to that of other Guzmania hybrids.

V. Blooming habit: Inflorescence rises from the center of the rosette of foliage to form a fountain-shaped spire approximately 41 cm. tall. The diameter of the floral stalk is approximately 2.5 cm. measured at the base of the stalk. The diameter of the inflorescence, including bracts, is approximately 16 cm. at the widest point.

A. *Scape bracts.*—Bright red, ranging from Royal Horticultural Society Color Card 42A through 45A and 45C. The blending of these shades of red creates a visual impression of vibrant color. The typically green stalk of the inflorescence is hidden from view by the colorfull brackts, heightening the visual impression. The lowermost scape bracts are approximately 10 cm. long and 8 cm. wide. The upper scape bracts are approximately 6 cm. long, and 6 cm. wide.

B. *Flowers.*—The flowers rarely emerge from the floral bracts located on the spikes which branch from the floral stalk. When visible, flower petals are yellow, Royal Horticultural Society Color Card 13C, and the corolla is pale beige-white. (The visual impression of flowering is created by the white-tipped spikes nestled within the scape bracts at the top of the inflorescence, even when no actual flowers emerge.)

VI. Foliage:

A. *Size.*—Lower-most leaves are approximately 26 cm. long, and are approximately 7.5 cm. wide at the base of the leaf, with the width narrowing to aproximately 2.5 cm. Upper leaves, upon reaching full length, are approximately 45 cm. and are approximately 9.0 cm. wide at the base, with the width narrowing to approximately 3.0 cm.

B. *Shape.*—Lanceolate with a rounded tip, not sharp; entire, smooth.

C. *Texture.*—Shiny, smooth.

D. *Color.*—Matte green, Royal Horticultural Society Color Card 147A, on the upper surface. The underside of the leaves is a paler green, Royal Horticultural Society Color Card 137A–137B. While in active growth, thin, pale reddish veins of an indeterminate shade appear on the underside of the mature leaves. These veins fade as blooming commences.

We claim:

1. A new and distinct variety of Guzmania named "Red Star", as illustrated and described.

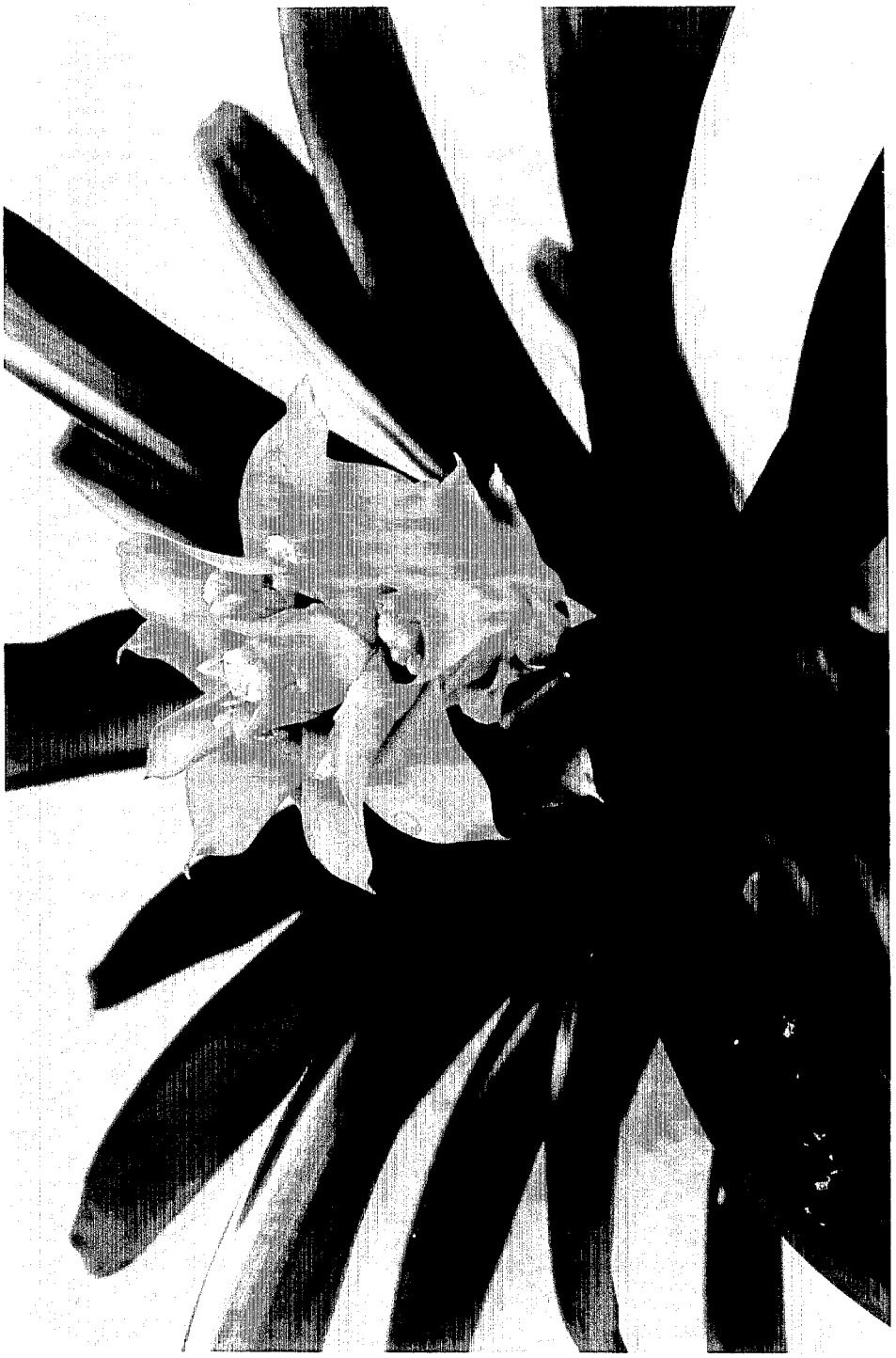

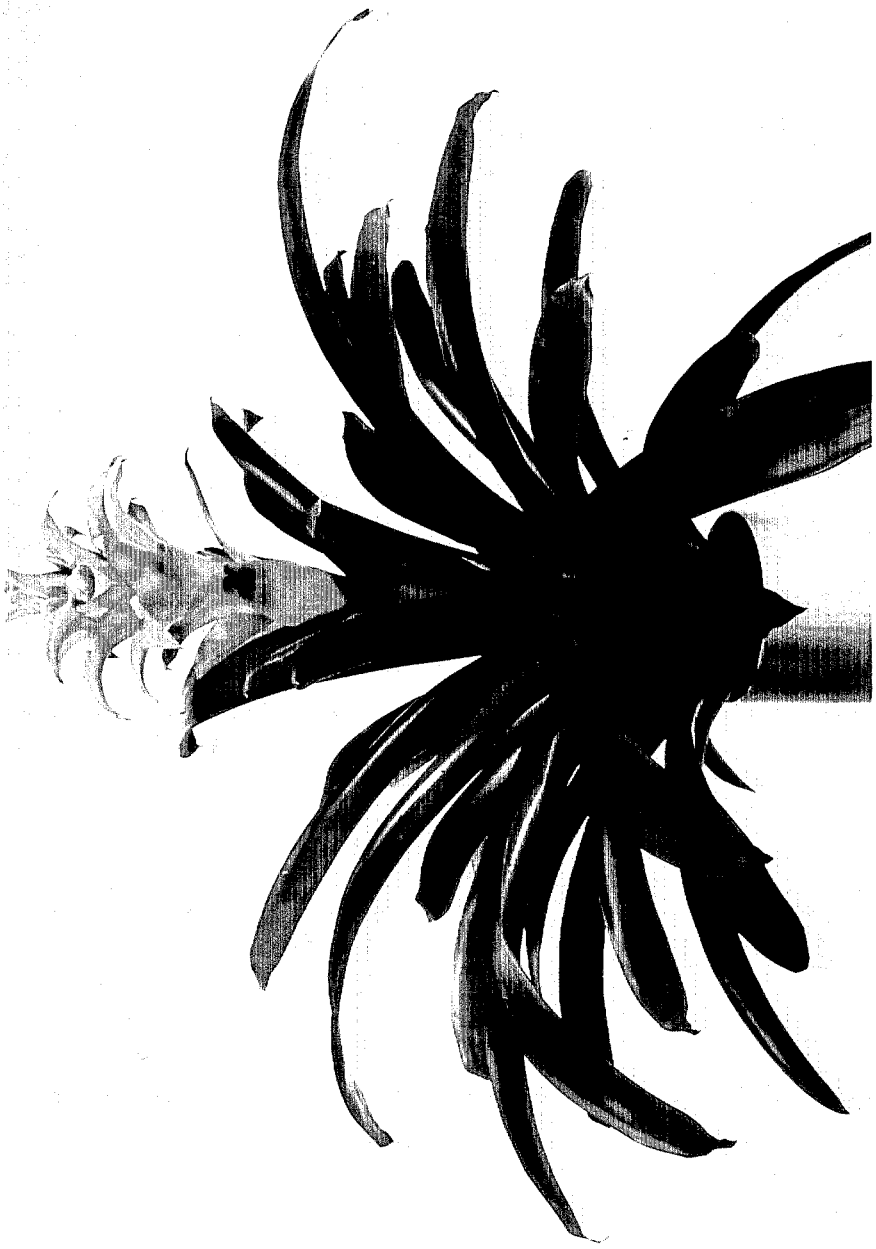

* * * * *